United States Patent
Suwalski et al.

(10) Patent No.: US 11,344,355 B2
(45) Date of Patent: May 31, 2022

(54) CARDIAC SURGERY CRYOPROBE

(71) Applicant: Medidata sp. z o.o., Warsaw (PL)

(72) Inventors: Piotr Suwalski, Warsaw (PL);
Choudhary Sanjeev, Warsaw (PL);
Cezary Górniak, Piastów (PL)

(73) Assignee: Medidata Sp. z o.o., Warsaw (PL)

( * ) Notice: Subject to any disclaimer, the term of this patent is extended or adjusted under 35 U.S.C. 154(b) by 589 days.

(21) Appl. No.: 16/192,799

(22) Filed: Nov. 16, 2018

(65) Prior Publication Data

US 2020/0100827 A1    Apr. 2, 2020

(51) Int. Cl.
*A61B 18/14*    (2006.01)
*A61B 18/02*    (2006.01)
(Continued)

(52) U.S. Cl.
CPC .......... *A61B 18/02* (2013.01); *A61B 18/1492* (2013.01); *A61B 2017/00084* (2013.01);
(Continued)

(58) Field of Classification Search
CPC ................ A61B 18/02; A61B 18/1492; A61B 2017/00084; A61B 2017/00243;
(Continued)

(56) References Cited

U.S. PATENT DOCUMENTS 3,692,029 A    9/1972    Adair
5,324,286 A    6/1994    Fowle
(Continued)

FOREIGN PATENT DOCUMENTS

EP    2533716 B1    8/2015
EP    2632363 B1    10/2015
(Continued)

*Primary Examiner* — Michael F Peffley
*Assistant Examiner* — Amanda L Zink
(74) *Attorney, Agent, or Firm* — Andrzej Malarz, Esq.

(57) ABSTRACT

A cryoprobe having a working tip formed of two coaxial flexible internal and external tubular lines, wherein the cross-section diameter of the internal line is substantially smaller than the cross-section diameter of the external line, and the length is slightly smaller than the length of the external line. The external line ends with a top closing the working tip of the cryoprobe, while the end of the internal line is open, and there are openings evenly distributed across the circumference on at least half of the section of the internal line. On the section from the handle to the end located under the top, a resistance wire is spirally wound on the internal line, wherein the distance between the wall of the external line and the wall of the internal line is larger than the diameter of the resistance wire. On the external line, no further from the top located on the top of the working tip than ⅓ of the length thereof, there is a temperature sensor connected to the handle by a power line. External and internal lines corresponding to the external and internal lines come out from the working tip outside the handle, wherein the external and internal lines together with the harness of power lines and, insulated with an insulating hose, are connected from the handle to the unit supplying air and liquid nitrogen at low pressure of up to 0.5 bars using a pump system.

11 Claims, 6 Drawing Sheets

(51) Int. Cl.
*A61B 17/00* (2006.01)
*A61B 18/00* (2006.01)

(52) U.S. Cl.
CPC .............. *A61B 2017/00243* (2013.01); *A61B 2018/00041* (2013.01); *A61B 2018/00351* (2013.01); *A61B 2018/00577* (2013.01); *A61B 2018/0212* (2013.01); *A61B 2018/0262* (2013.01)

(58) Field of Classification Search
CPC  A61B 2018/00041; A61B 2018/00351; A61B 2018/00577; A61B 2018/00791; A61B 2018/00875; A61B 2018/0212; A61B 2018/0262
See application file for complete search history.

(56) References Cited

U.S. PATENT DOCUMENTS

| | | | |
|---|---|---|---|
| 6,383,181 | B1 | 5/2002 | Johnston et al. |
| 6,562,030 | B1 | 5/2003 | Abboud et al. |
| 2002/0099364 | A1* | 7/2002 | Lalonde ................. A61B 18/02 606/21 |
| 2003/0014095 | A1* | 1/2003 | Kramer .................. A61B 18/02 607/106 |
| 2010/0249766 | A1 | 9/2010 | Saadat |
| 2012/0265186 | A1* | 10/2012 | Burger .................. A61B 18/02 606/21 |
| 2013/0253491 | A1* | 9/2013 | Burr .................... A61B 18/0218 606/21 |
| 2014/0350537 | A1 | 11/2014 | Baust et al. |
| 2015/0265330 | A1 | 9/2015 | DeLonzor et al. |
| 2015/0282858 | A1 | 10/2015 | Baust et al. |
| 2016/0354134 | A1 | 8/2016 | Pageard et al. |
| 2020/0069354 | A1* | 3/2020 | Bockenstedt ...... A61B 18/1206 |
| 2020/0085485 | A1* | 3/2020 | Skorich ................. A61B 18/02 |
| 2020/0297403 | A1* | 9/2020 | Kochavi ............ A61B 18/0218 |

FOREIGN PATENT DOCUMENTS

| | | |
|---|---|---|
| EP | 3115011 A1 | 1/2017 |
| EP | 3062721 B1 | 3/2019 |
| JP | 5684810 B2 | 3/2015 |
| WO | 9634571 A1 | 11/1996 |
| WO | 2011142909 A1 | 11/2011 |

\* cited by examiner

CARDIAC SURGERY CRYOPROBE

CROSS-REFERENCE TO RELATED APPLICATIONS

This nonprovisional application claims priority under 35 U.S.C. 119, to European Patent Application No. 18197511, filed on Sep. 28, 2018, the contents of each is hereby incorporated by reference.

BACKGROUND OF THE INVENTION

Field of the Invention

The invention relates to a low-pressure, flexible cardiac surgery cryoprobe with active thawing and electrical conductivity measurement system, intended for local freezing of tissues, in particular of heart tissue during a cardiac surgery.

Description of Related Art Including Information Disclosed Under 37 CFR 1.97 and 1.98

The invention is to be used for performing cryoablation of atria of the heart as part of the treatment of arrhythmias, primarily of atrial fibrillation. The invention is intended for endo- and epicardial ablation, mainly by way of minithoracotomy.

Surgical ablation of the so-called concomitant atrial fibrillation is considered to be the treatment of choice when performing other cardiac surgery procedures, most often of mitral valve repair or replacement. The method is recommended in Polish, European and American guidelines for treatment procedures developed by recognised cardiac surgery and cardiology societies.

Cryothermy, as the oldest and most extensively studied method of exposing tissues to an energy source, is also used for heart tissue ablation. Cryoablation is based on removing thermal energy from the target tissue, which results in the death of myocytes and the subsequent formation of a scar in the low temperature exposure site. The essence and the objective of the therapy of this type, i.e. treatment of the most common arrhythmia, that is atrial fibrillation, is the formation of a precisely located scar of appropriate shape, which, unlike heart muscle cells, does not conduct cellular currents. This treatment using cryotherapy is more effective and far safer compared to treatment using high temperatures, i.e. for instance, radio frequency current, where a number of cases was described of damage to adjacent organs, i.e. oesophagus and coronary arteries.

Commercially available cryothermy devices are mainly based on compressed argon which, in many countries, including Poland, is very expensive, and which, in many countries, also including Poland, is not readily available. The second most commonly used gas is nitrous oxide, which is also expensive, without, however, ensuring the achievement of temperatures as low as in the case of argon. Operation of most, if not all, currently used flexible cryoprobes is based on the Joule-Thomson effect, i.e abrupt expansion of gas with initial pressure of up to 300 bars in the closed space of the probe, which is definitely less safe than using a low pressure gas.

Application US2016354134 (A1) discloses a multi-function device for performing cardiac, i.e. percutaneous/transcathetral ablation. The device is intended both as a cannula blocking blood flow through the pulmonary vein and as a cryoprobe.

European Patent No. 2 632 363 protects a solution designed for the ablation procedure performed both by radio frequency current and cryothermy. Accordingly, the device is equipped with lines for supplying a cooling liquid and with an electrode array.

European application EP 3062721 (A1) discloses a device for cryoablation equipped with a tissue temperature measurement system composed of a series of thermocouples. The device allows for assessing the depth of heart muscle tissue damage by performing multiple temperature measurements using one or more thermocouples, determining the temperature shift rate for each one or more of the thermocouples and adjusting the temperature of the probe in contact with heart muscle tissue when temperature shift rate is changed.

U.S. Pat. No. 6,383,181, relating to an apparatus and a method for cryothermally treating pre-cancerous gastrointestinal tissue, describes the use of low pressure liquid nitrogen. Liquid nitrogen is sprayed directly on the affected tissue fragment from a probe inserted to the gastrointestinal tract through an endoscope.

Also, WO9634571 (A1) discloses a device for thermoablation equipped with a cooling tip designed to quickly lower the temperature of the tissue previously damaged by high temperature.

The inventors intended to design an elastic low pressure cryoprobe for minimally invasive cardiosurgical ablation using videothoracoscopic technologies, wherein the new feature of the probe was to be active thawing allowing for safe detachment of the tip of the probe from the tissue and intrasurgical passive and active readout of the potentials to confirm proper conduction of electrical pulses. The shape and size of the cryoprobe were designed based on clinical trials and they allow for precision manipulation and cryoapplication within the left and right atria of the heart.

BRIEF SUMMARY OF THE INVENTION

The essence of the solution according to the invention is that the cryoprobe has a working tip arranged in a gun-shaped handle, wherein the working tip is formed of two coaxial flexible internal and external tubular lines, and the cross-section diameter of the internal line is substantially smaller than the cross-section diameter of the external line, and the length is slightly smaller than the length of the external line. The external line ends with a top closing the working tip of the cryoprobe, while the end of the internal line is open. There are openings evenly distributed across the circumference on at least half of the section of the internal line located in the working tip of the cryoprobe. A resistance wire is spirally wound on the internal line, wherein the distance between the wall of the external line and the wall of the internal line is larger than the diameter of the resistance wire. On the external line, no further from the top located on the top of the working tip than ⅓ of the length thereof, there is a temperature sensor connected to the handle by a supply line. Additionally, there is a socket inside the handle in which the working tip of the cryoprobe is arranged, to which the power lines are connected, supplying voltage to both the resistance wire and the walls of the external line. The external line connected to the voltage is a measuring electrode, and external and internal lines corresponding to the external and internal lines in the working tip come out from the socket outside the handle, which together with the harness of power lines, insulated with an insulating hose, are connected from the handle to the unit supplying air and liquid nitrogen at low pressure from 0.1 to 6 bars.

Preferably, the internal and external lines are made of metal.
Preferably, the internal and external lines are made of copper or alloys thereof.
Preferably, the internal and external lines are made of aluminum or alloys thereof.
Preferably, the diameter of the openings is variable and it increases towards the top.
Preferably, here is a limiting sleeve directly below the working tip of the cryoprobe.

In a preferred embodiment, there is a double-layer, rigid, partially movable thermal jacket on the external line.

Preferably, the thermal jacket consists of two coaxial, rigid tubes that are longitudinally movable one relative to the other, wherein the tube having a larger cross-section is stabilized with one end thereof in the handle.
Preferably, the external line is a measuring electrode for testing electrical flows in tissues.
Preferably, the external line (3) is constructed of interconnected coaxial rings.
Preferably, the pressure at which air and liquid nitrogen are supplied to the working tip is from 0.5 to 3 bars.

The invention is advantageous in that the flexible active working tip enables the surgeon to shape the probe freely and with high precision, which in turn enables faster and more thorough ablation and a smaller number of applications required to achieve a complete pattern of ablation lines. The advantage achieved with this solution is the reduced duration of cardiac arrest and the resultant increased patient's safety. Also, an important feature of the solution is the combination of a low-pressure cryoprobe with the flexibility of the working tips, which according to the invention, is provided by the selection of suitable materials or the appropriate design of the active tip of the cryoprobe. Proper operation of the cryoprobe greatly relies on the presence of a resistance wire spirally wound on the internal line that has a number of functions. In addition to the primary function of heating the air inside the internal line, the wire allows for maintaining the minimum distance required between the internal and external lines, thus maintaining the space between the lines unobstructed, and it also prevents the working tip of the cryoprobe from breaking, kinking and bending excessively.

The operation of the low-pressure cryoprobe is based on the use of liquid nitrogen at a pressure of 0.1 to 6 bars to cool the tissue, which is highly important for patient's safety. The advantage of using liquid nitrogen as a cooling medium in the process of performing ablation procedure is the possibility of achieving a lower temperature of the working tip of the cryoprobe compared to other media, and, consequently, faster cooling of heart tissue.

A further advantage of the cryoprobe according to the invention is the possibility of controlling the process of thawing of the cryoprobe frozen to the tissue, without the risk of hibernating the tissue and breaking the frozen tissue.

The solution according to the invention is also characterised by the possibility of validating the ablation performed without the need to change working tips. In accordance with European and American standards, performance of effective ablation is confirmed by measuring the electrical conductivity of the ablated tissue. This requires the use of separate devices, as well as repeated insertion and removal of the latter through the surgical wound to heart tissue. Integrating the cryoprobe and a measuring device in one working tip will enable the verification of the efficiency of the ablation performed by performing electrical measurements (of electrical conductivity) without the need to change the devices or the working tip.

Moreover, a number of factors affect the temperature of the active part of the cryoprobe during ablation. Enabling the measurement of actual temperature of the active tip of the cryoprobe according to the invention has a positive effect on the ablation efficiency (control of residence time of ablated tissue in the "death zone") and it will make it possible to shorten the duration of ablation and to adjust the ablation parameters to a particular patient and thus increase the efficiency of the procedure.

Manipulating the active flexible working tip using a low pressure gas, as is the case in the present invention, affects the cryoablation outcome, and, consequently:
  it reduces the duration of the surgery;
  it increases patient's safety (e.g. it reduces the risk of breaking the frozen tissue, reduces the residence time of heart tissue in the death zone)
  it eliminates the need to change working tips, and, as a result, it does not distract the cardiac surgeon, it reduces the duration of the surgery and lowers the risk of infection in the patient;
  it facilitates manual mastering of the cryoprobe, as it is easier to learn to manipulate one rather than several working tips, which lowers the risk of the surgery;
  it ensures firm and complete adhesion of the working tip, thus ensuring the continuity of ablation lines;
  it increases ablation efficiency.

BRIEF DESCRIPTION OF THE SEVERAL VIEWS OF THE DRAWINGS

The solution according to the invention is shown in the embodiments in the drawing, in which.

DETAILED DESCRIPTION OF THE INVENTION

Figure 1A:
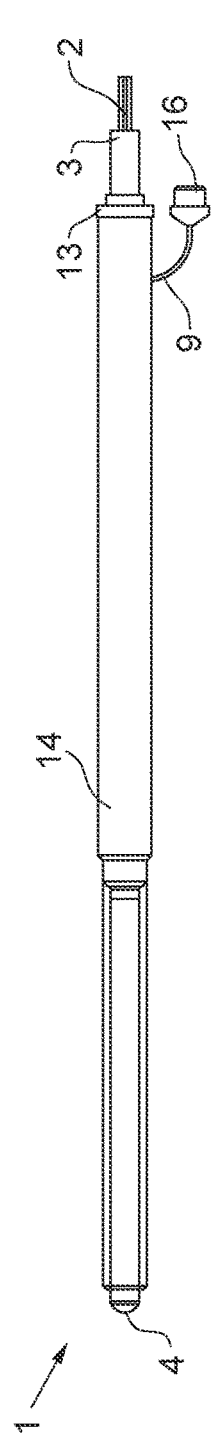
FIG. 1 is a projection of the working tip with the thermal jacket closed and opened: a) in side view, b) of the working tip in longitudinal section, c) of the working tip in half-view/half-section, d) of the working tip in half-view/half-section.
Figure 1B:
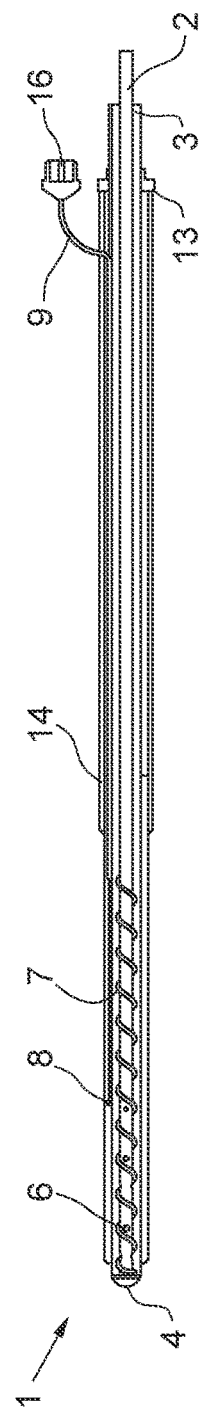
Figure 1C:
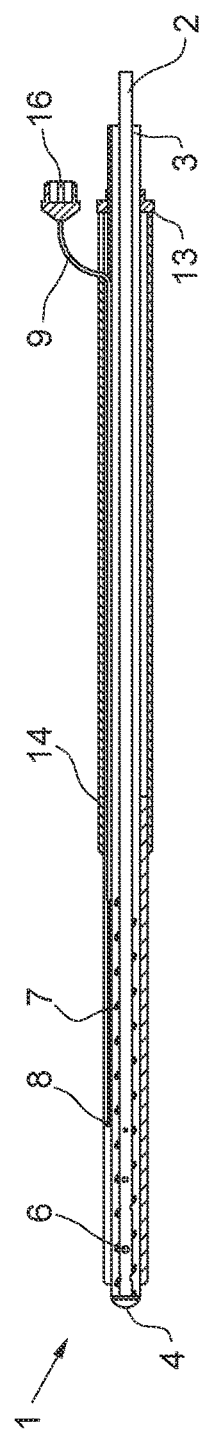
Figure 1D:
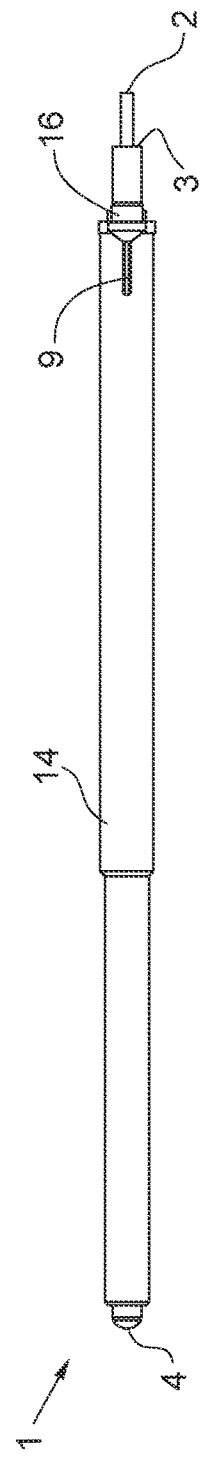
Figure 2:
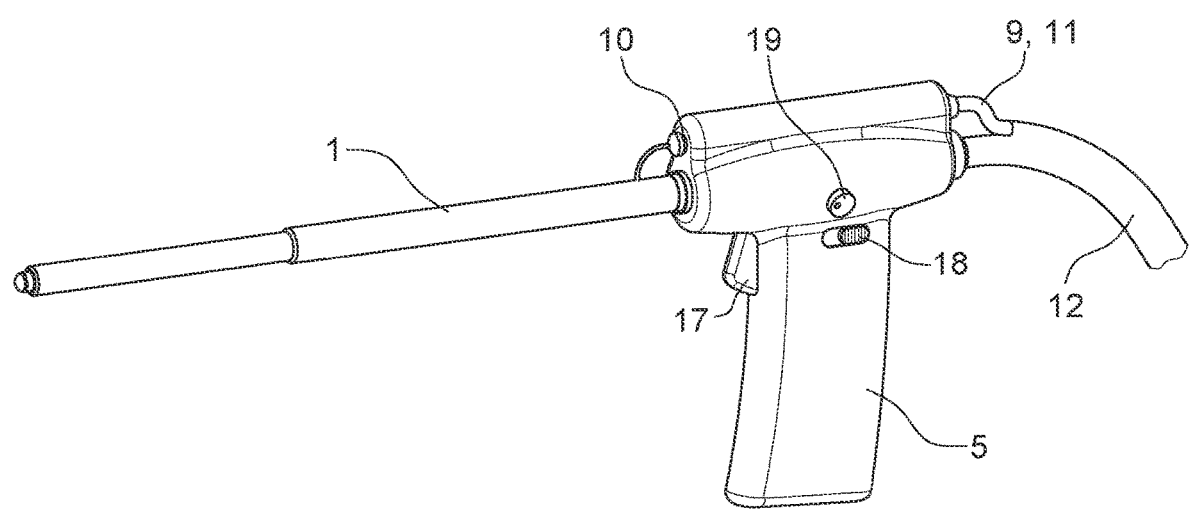
FIG. 2 is a view of the handle with the working tip.
Figure 3A:
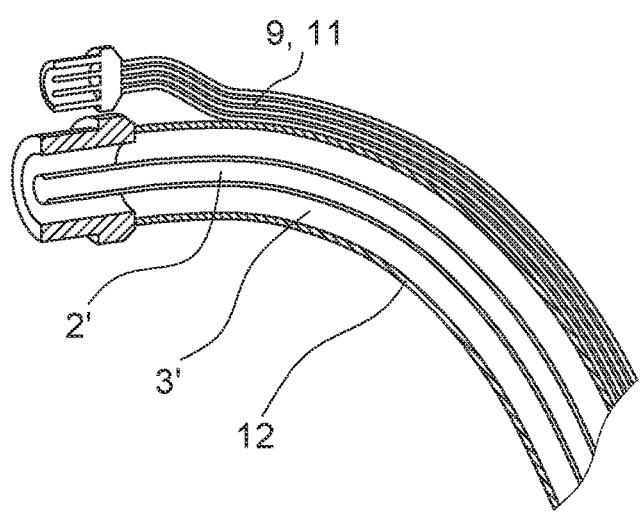
FIG. 3 is a cross-section of the working tip with a line supplying voltage to the temperature meter.
Figure 3B:
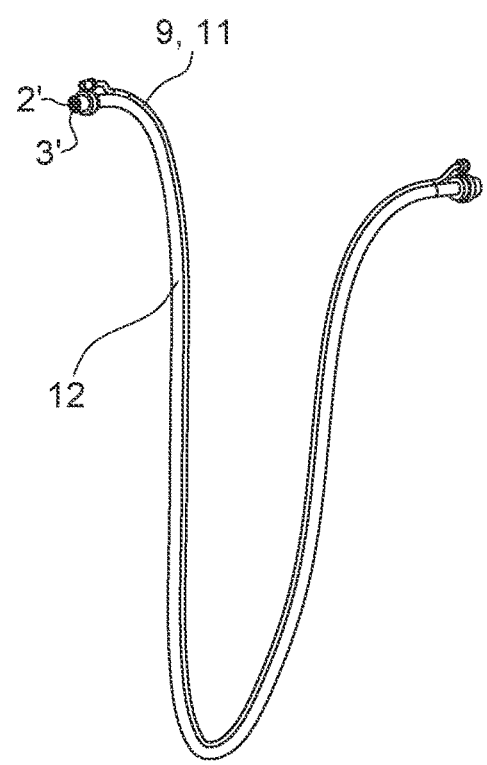
Figure 4:
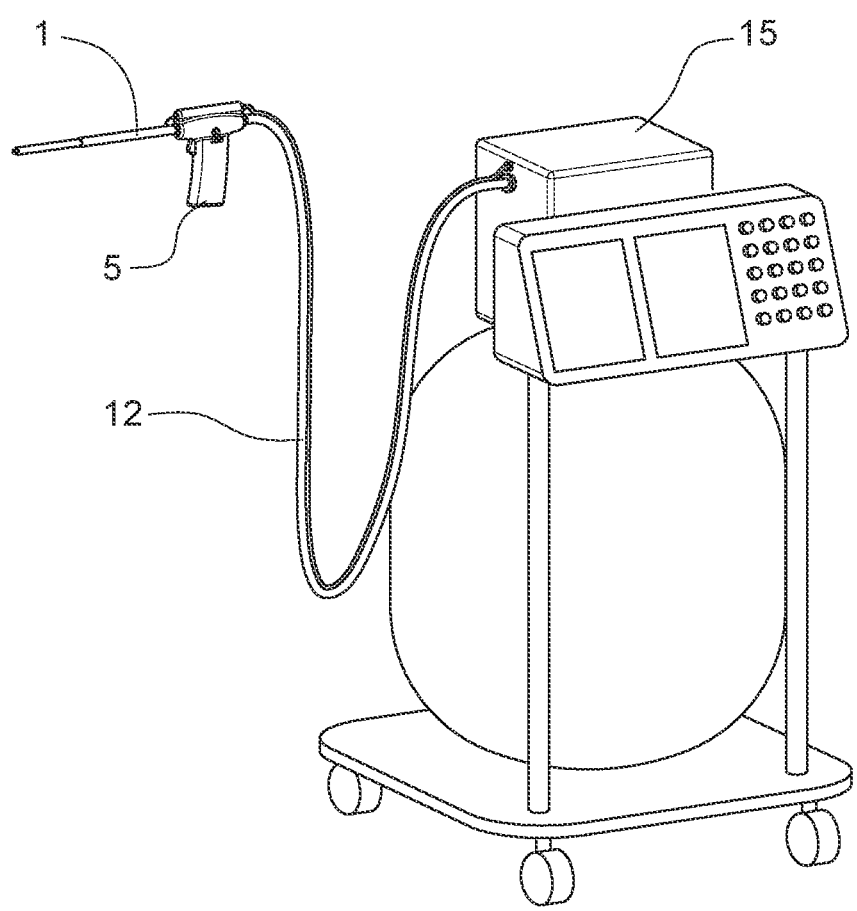
FIG. 4 is a view of the unit with the cryoprobe.
Figure 5A:
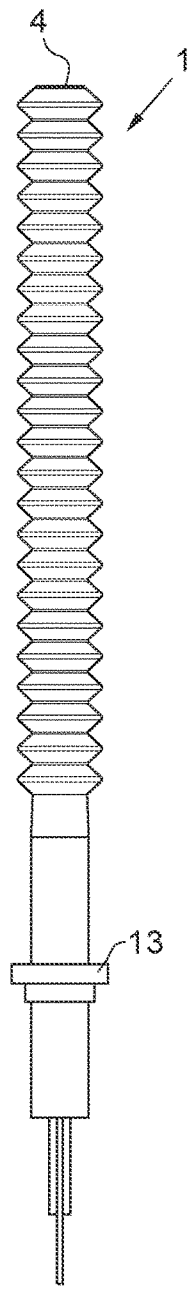
FIG. 5 is a projection of a variant of the working tip in four views and half-view/half-sections without a thermal jacket, for better illustration of the design of the tip.
Figure 5B:
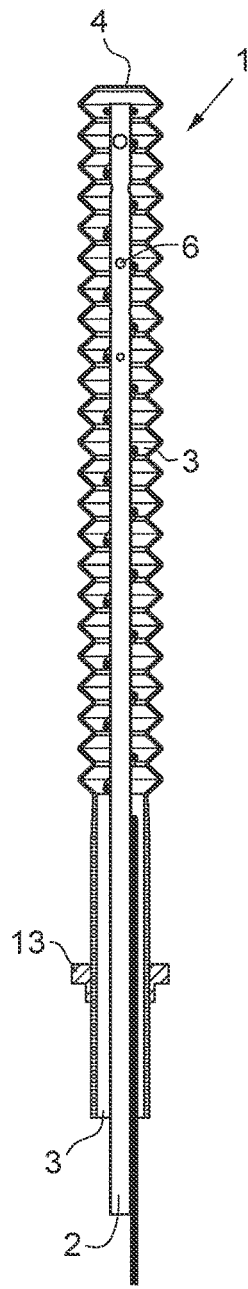
Figure 5C:
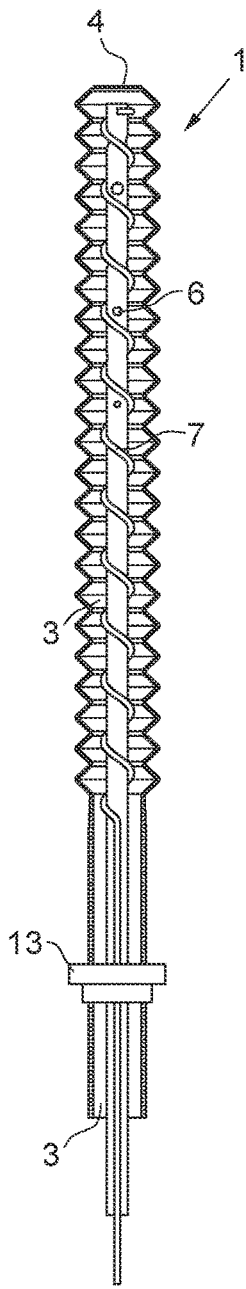
Figure 5D:
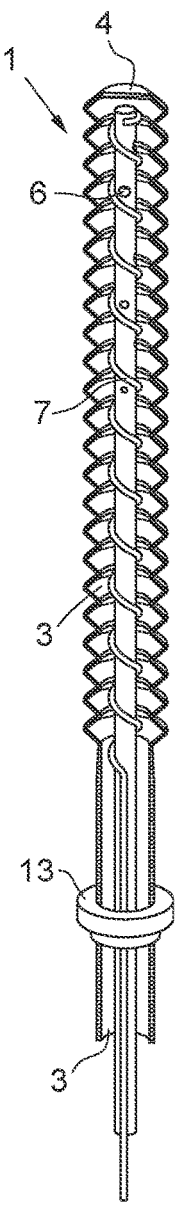

In the working part, the cardiac surgery cryoprobe has a working tip 1 mounted from a gun-shaped handle 5 connected to a unit 15, equipped with pumps supplying alternately liquid nitrogen and air to the working end 4. The working tip 1 is constructed of two metal coaxial flexible tubular internal 2 and external 3 lines, to which gas or air is supplied and discharged from. The cross-section diameter of the internal line 2 is substantially smaller than the cross-section diameter of the external line 3, and the length is slightly smaller than the length of the external line 3, so that the open end of the internal line 2 is not in contact with the top 4 closing the working tip 1 of the cryoprobe.

There are openings 6 evenly distributed across the circumference on at least half of the section of the internal line 3 located in the working tip 1 of the cryoprobe. The diameter of the openings 6 is variable and it increases towards the top 4. When liquid nitrogen flows through the internal line 2, a part thereof leaks to the space between the internal 2 and external 3 lines, and only a part reaches the top 4. This results in homogeneous temperature within the working tip 1.

A resistance wire 7 is spirally wound on the internal line 2 in the working tip 1, connected in the handle 5 with the power line. The resistance wire 7 heats the air that pushes liquid nitrogen from the internal line 2, it prevents the walls of the internal line 2 from contacting the walls of the external line 3, which would obstruct the openings 6 and would obstruct the space between the internal 2 and external 3 lines, and it protects the walls of the internal line 2 against kinking or breaking.

On the external line 3, no further from the top located on the top of the working tip 1 than ⅓ of the length thereof, there is a temperature sensor 8 connected to the handle 5 by a power line 9. The line 9 ends with a plug arranged in the socket 16 located in the handle 5, over the inlet of the shaft 1.

Inside the handle 5 there is a socket 10, in which the working tip 1 of the cryoprobe is arranged, and power lines 11 are connected to the socket. Power lines 11 supply voltage to the resistance wire 7 and to the walls of the external line 3. External 3' and internal 2' lines corresponding to the external 3 and internal 2 lines run from the socket 10 outside the handle. External wires 3 'and inner 2' together with a harness of power wires 9 and 11 secured by insulating hose 12 are led from handle 5 to supply unit 15 air and liquid nitrogen at low pressure from 0.1 to 6 Bars, preferably from 0.5 to 3 Bars.

On the external line 3, on the section from the handle 5 to the working tip, there is a thermal jacket 14 provided. The thermal jacket 14 consists of two coaxial, rigid tubes that are longitudinally movable one relative to the other, wherein the tube having a larger cross-section is stabilized with one end thereof in the handle 5. The thermal jacket 14 renders the working tip rigid over the desired length, it is designed to reduce thermal losses within the shaft, it prevents accidental over-freezing of the tissue adjacent to the ablation site. Additionally, it constitutes the electrical insulation of the shaft, while the external line 3 acts as an electrode.

There is a limiting sleeve 13 directly below the working tip 1 of the cryoprobe.

The internal 2 and external 3 lines can be made of copper or aluminum or alloys 5 thereof, which provides suitable elasticity and flexibility.

In the second embodiment shown in FIG. 5, the flexibility of the working tip 1 is achieved through a specific construction of the external line 3, which can take the form of interconnected coaxial rings.

There are switches on the handle 5 to control the cryoprobe. One of them, designated with number 17, arranged on the conventional site of the gun trigger, when pulled, activates the flow of liquid nitrogen to the internal line 2. Switch 17 is operated with the index finger.

Where the thumb reclines against the surface of the handle 5, there is a switch 18 designed to turn the flow of air to the internal line 2 on and off and to activate the flow of current to the resistance wire 7.

Slightly above there is another switch 19 used to activate the flow of current to the wall of the external line 3, which result in the external line 3 becoming an electrode for electrical stimulation, i.e. pacing and sensing.

Figure 6:
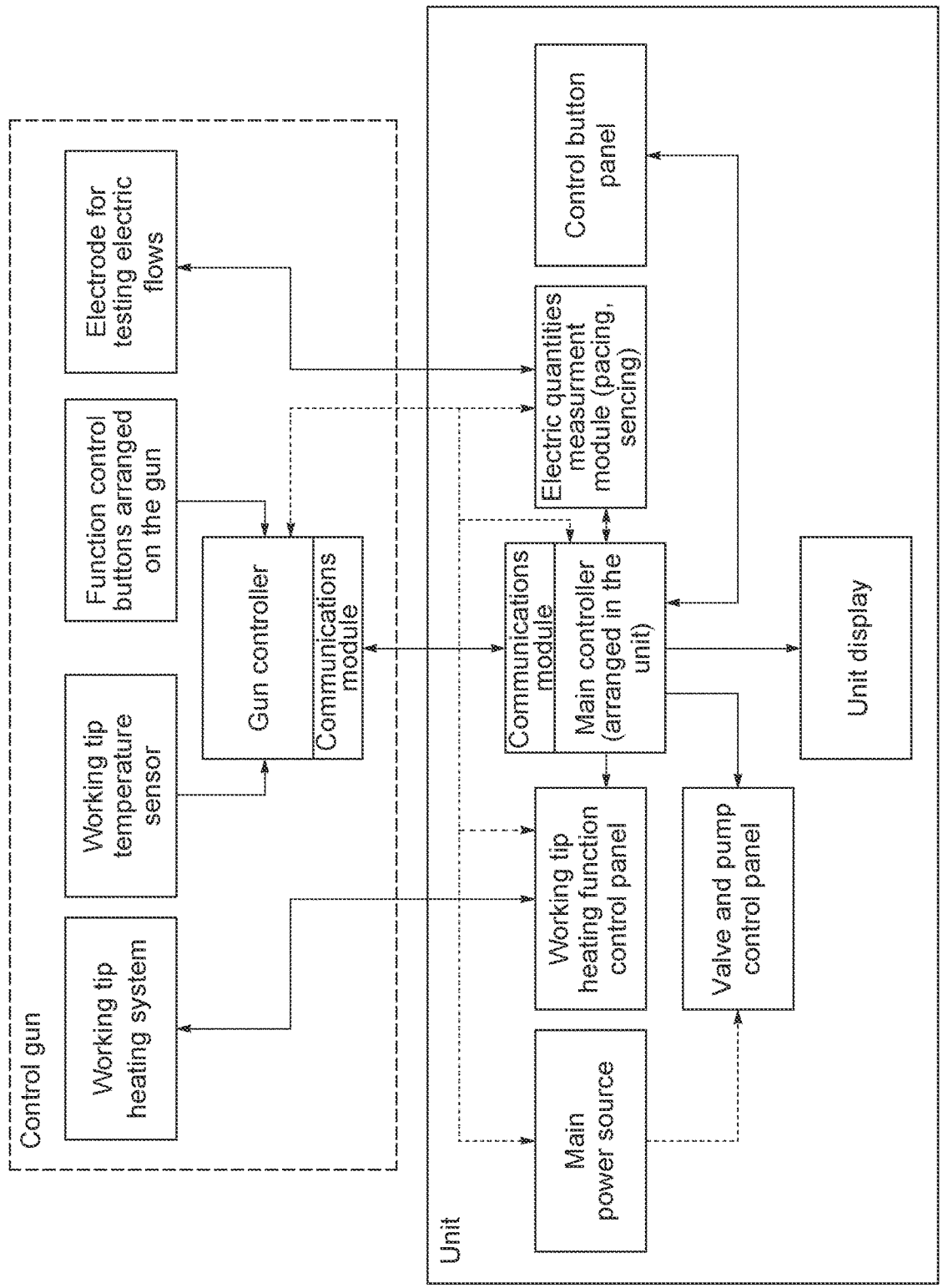
FIG. 6 is a modular scheme of the power supply and control system.

The device according to the invention is powered and controlled by a power and control system schematically shown in FIG. 6.

The operation of the cryoprobe consists in that the pressing of the switch 17 activates the flow of liquid nitrogen through the internal line 2' to the internal line 2. The gas diffuses within the internal line 2 and it partly flows to the space between the internal line 2 and the external line 3 to reach the top 4. After reaching the desired temperature and freezing the tissue, switch 18 is used to activate the flow of air to the internal line 2 and the heating thereof by the resistance wire 7. Heated air pushes the liquid nitrogen from the space inside the internal 2 and external 3 lines and it reaches the top 4, which it heats to a temperature slightly above 0° C. The external surface of the top 4 frozen to the tissue heats the ablation site, so that can it easily be detached from the frozen tissue. Then, the switch 19 is used to activating the supply of voltage to the walls of the external line 3 and a tissue electrical conductivity measurement is performed. If the outcome of the stimulation and conductivity detection is unsatisfactory, the entire process is repeated.

LIST OF REFERENCE NUMERALS

1—Working tip
2—Internal line
3—External line
4—Top
5—Handle
6—Hole
7—Resistance wire
8—Temperature sensor
9—Supply line
10—Socket
11—Power line
12—Isolating hose
13—Sleeve
14—Thermal jacket
15—Unit
16—Socket
17—Switch
18—Switch
19—Switch

The invention claimed is:

1. A cardiac surgery cryoprobe comprising a working tip (1) mounted in a gun-shaped handle (5) equipped with at least one switch connected to a unit (15), having a tubular line through which a cooling medium is supplied to the working tip,
   wherein the working tip (1) is formed of two coaxial flexible tubular internal (2) and external (3) lines,
   wherein the internal line (2) has a cross-section diameter that is substantially smaller than the cross-section diameter of the external line (3), and a length that is slightly smaller than the length of the external line (3),
   wherein the external line (3) ends with a top (4) closing the working tip (1) of the cryoprobe, while the end of the internal line (2) is open, and
   the internal line (2) has openings (6) evenly distributed across the circumference on at least half of the section of the internal line (2), and
   a resistance wire (7) is spirally wound along a wall of the internal line (2), wherein the distance between the wall of the external line (3) and the wall of the internal line (2) is larger than the diameter of the resistance wire (7),
   on the external line (3), no further from the top (4) located on the top of the working tip (1) than ⅓ of the length thereof, there is a temperature sensor (8) connected to the handle (5) by a power line (9), and inside the handle (5) there is a socket (10), in which the working tip (1) of the cryoprobe is mounted, to which the power lines (11) are connected, the power lines (11) supplies voltage to both the resistance wire (7) and the walls of the external line (3), wherein the external line (3) is a measuring electrode when the external line (3) is supplied with voltage, and extension part external line (3') and extension part internal line (2') extend continuously corresponding to the external line (3) and internal line (2) of the working tip (1), respectively, and the extension part external line (3') and the extension part internal line (2') extend from the socket (10) and toward outside the handle, wherein the extension part external line (3') and the extension part internal line (2') are insulated with an insulating hose (12) together with the harness of the power line (9) and the power line (11), the extension part external line (3') and the extension part internal line (2') extend outside from the handle (5) and are connected to the unit (15), and wherein the extension part external line (3') and the extension part internal line (2') supply air and liquid nitrogen at low pressure of 0.1 to 6 bars using a pump system.

2. The cryoprobe according to claim 1, wherein the internal (2) and external (3) lines are made of metal.

3. The cryoprobe according to claim 2, wherein the internal (2) and external (3) lines are made of copper or alloys thereof.

4. The cryoprobe according to claim 2, wherein the internal (2) and external (3) lines are made of aluminum or alloys thereof.

5. The cryoprobe according to claim 1, wherein the diameter of the openings (6) varies so as to increase towards the top (4).

6. The cryoprobe according to claim 1, wherein external line (3) is a measuring electrode for testing electrical flows in tissues.

7. The cryoprobe according to claim 1 wherein there is a double-layer, partially movable rigid thermal jacket (14) on the external line (3).

8. The cryoprobe according to claim 6 wherein a thermal jacket (14) consists of two coaxial, rigid tubes that are longitudinally movable one relative to the other, wherein the tube having a larger cross-section is stabilized one end thereof in the handle (5).

9. The cryoprobe according to claim 1 wherein external line (3) is a measuring electrode for testing electrical flows in tissues.

10. The cryoprobe according to claim 1, wherein external line (3) is constructed of interconnected coaxial rings.

11. The cryoprobe according to claim 1, wherein the pressure at which air and liquid nitrogen are supplied to the working tip is from 0.5 to 3 bars.

* * * * *